United States Patent [19]

Lalani

[11] Patent Number: 5,545,480
[45] Date of Patent: Aug. 13, 1996

[54] DENTAL FLOSS

[76] Inventor: Abdul H. Lalani, Richmond Centre Dental Clinic, Richmond Centre Mall, North Wing 1940-6060 Minoru Blvd., Richmond, B.C., Canada, V6Y 2V7

[21] Appl. No.: 403,152

[22] Filed: Mar. 13, 1995

[51] Int. Cl.$^6$ .................................................. D02G 3/00
[52] U.S. Cl. ........................ 428/364; 428/399; 132/321
[58] Field of Search ............................ 132/321; 428/364, 428/399

[56] References Cited

U.S. PATENT DOCUMENTS

| | | | |
|---|---|---|---|
| 1,752,990 | 4/1930 | Jeandheur | 428/399 |
| 2,133,322 | 10/1938 | Cupery | 428/399 |
| 3,127,915 | 4/1964 | Bottomley | 428/399 |
| 3,185,613 | 5/1965 | Adams | 428/399 |
| 3,699,979 | 10/1972 | Muhler et al. | 132/321 |
| 4,142,538 | 3/1979 | Thorton | 132/321 |
| 4,974,615 | 12/1990 | Doundoulakis | 132/321 |
| 4,986,288 | 1/1991 | Kent et al. | 132/321 |
| 5,159,943 | 11/1992 | Richards et al. | 132/321 |
| 5,316,028 | 5/1994 | Flemming | 132/321 |

*Primary Examiner*—N. Edwards

[57] ABSTRACT

A length of dental floss having a series of spaced members of different sizes along the length. In the preferred embodiment, the size of the spaced members increase by regular increments from one end.

2 Claims, 1 Drawing Sheet

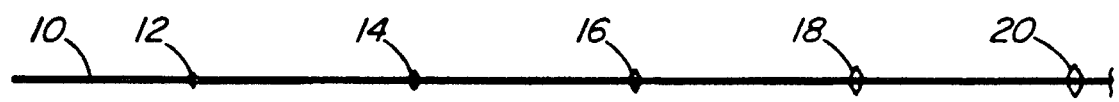

DENTAL FLOSS

FIELD OF THE INVENTION

This invention relates to dental floss.

DESCRIPTION OF THE PRIOR ART

Dental floss is strongly recommended for the daily care of teeth. Cleaning by a brush with toothpaste is, of course, much longer established but it is now recommended that dental floss be used as well as brushing. The dental floss clears the spaces between the teeth in a manner that a toothbrush, with or without toothpaste, cannot do.

Dental floss is also used by dentists during routine dental work, such as fillings, and during orthodontic work in which teeth are built up. It is important that the appropriate spaces be left between the teeth and therefore, before filling material has set, the dentist will use dental floss of the appropriate diameter to clear that space.

Generally a dentist has dental floss of differing diameters. People have differing gaps between their teeth, and even in one individual the gap between various teeth will differ depending on a number of factors, for example the position of the teeth in the mouth.

The selecting of the various diameters of dental floss can be a nuisance. Filling material can set quite quickly and it is necessary for the dentist to act correspondingly quickly if the gap is to be properly formed.

It is known to tie a knot in the dental floss to achieve the desired diameter. But tying a knot is time consuming and the resulting diameter may not be exactly as desired.

SUMMARY OF THE INVENTION

The present invention avoids the necessity of having large numbers of pieces of dental floss of different diameter and the tying of knots. Instead the present invention permits the use of a single length of dental floss having members of different diameter formed on it.

Accordingly, the present invention is a length of dental floss having a series of spaced members of different size along said length.

DESCRIPTION OF THE DRAWINGS

The invention is illustrated in the single drawing which is a side elevation of a length of dental floss according to the present invention.

DESCRIPTION OF THE PREFERRED EMBODIMENTS

The dental floss according to the present invention is a length 10 of dental floss, of conventional material, having formed on it a plurality of spaced members 12, 14, 16, 18, 20 of differing size. In FIG. 1 the size increases by regular increments, the smallest member 12 is on the left and the largest member 20 on the right. The spaced members 12 to 20 are regularly spaced.

The spaced members may be formed by forming knots in the dental floss but are preferably formed when the floss is manufactured by building the spaced members 12 to 20 into the length 10 of dental floss.

To use the dental floss according to the present invention, the dentist simply picks the member 12, 14, 16, 18 or 20 of the appropriate diameter. The whole length of dental floss may then be inserted in the mouth of the patient but only the member of the appropriate diameter is worked back and forth between the teeth of the patient to secure the proper spacing.

The invention is simple to manufacture and yet provides, in a single short length, all that is required to provide adequate spacing for a large number of patients without the necessity to resort to stocking a wide variety of lengths of dental floss. No time need be wasted typing knots in the dental floss.

Although the forgoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

I claim:

1. A length of dental floss having first and second ends and having a series of spaced members along its length, said spaced members being of the same material as the reminder of the dental floss and increasing in size with distance from the first end of the length of dental floss.

2. A length of dental floss as claimed in claim 1 in which the spaced members are evenly spaced.

* * * * *